US012186397B2

(12) United States Patent
Huang

(10) Patent No.: US 12,186,397 B2
(45) Date of Patent: Jan. 7, 2025

(54) ADHESIVE CELL TISSUE GELS

(71) Applicant: National Cheng Kung University, Tainan (TW)

(72) Inventor: Lynn L. H. Huang, Tainan (TW)

(73) Assignee: National Cheng Kung University, Tainan (TW)

( * ) Notice: Subject to any disclaimer, the term of this patent is extended or adjusted under 35 U.S.C. 154(b) by 0 days.

(21) Appl. No.: 16/173,769

(22) Filed: Oct. 29, 2018

(65) Prior Publication Data

US 2019/0060465 A1     Feb. 28, 2019

Related U.S. Application Data

(63) Continuation-in-part of application No. 14/146,260, filed on Jan. 2, 2014, now abandoned, which is a
(Continued)

(51) Int. Cl.

| | |
|---|---|
| *A61K 47/34* | (2017.01) |
| *A61K 38/18* | (2006.01) |
| *A61K 38/19* | (2006.01) |
| *A61K 38/30* | (2006.01) |
| *A61L 24/00* | (2006.01) |
| *A61L 24/08* | (2006.01) |
| *A61L 24/10* | (2006.01) |
| *A61L 27/20* | (2006.01) |
| *A61L 27/22* | (2006.01) |

(Continued)

(52) U.S. Cl.
CPC .............. *A61K 47/34* (2013.01); *A61K 38/18* (2013.01); *A61K 38/1808* (2013.01); *A61K 38/1816* (2013.01); *A61K 38/1825* (2013.01); *A61K 38/1833* (2013.01); *A61K 38/1841* (2013.01); *A61K 38/185* (2013.01); *A61K 38/1858* (2013.01); *A61K 38/1866* (2013.01); *A61K 38/1875* (2013.01); *A61K 38/193* (2013.01); *A61K 38/30* (2013.01); *A61L 24/0005* (2013.01); *A61L 24/0015* (2013.01); *A61L 24/0031* (2013.01); *A61L 24/08* (2013.01); *A61L 24/102* (2013.01); *A61L 24/104* (2013.01); *A61L 24/108* (2013.01); *A61L 27/20* (2013.01); *A61L 27/222* (2013.01); *A61L 27/227* (2013.01); *A61L 27/24* (2013.01); *A61L 27/38* (2013.01); *A61L 27/3834* (2013.01); *A61L 27/44* (2013.01); *A61L 27/52* (2013.01); *A61L 27/54* (2013.01); *C08B 11/02* (2013.01); *C08B 11/12* (2013.01); *C08B 15/005* (2013.01); *C08B 15/10* (2013.01); *C08B 37/003* (2013.01); *C08B 37/0039* (2013.01); *C08B 37/0042* (2013.01); *C08B 37/0063* (2013.01); *C08B 37/0069* (2013.01); *C08B 37/0072* (2013.01); *C08B 37/0075* (2013.01); *C08B 37/0084* (2013.01); *C08G 12/46* (2013.01); *C08H 1/00* (2013.01); *C08H 1/06* (2013.01); *C08L 5/08* (2013.01); *C08L 89/06* (2013.01); *C09J 105/08* (2013.01); *C12N 5/0068* (2013.01); *A61L 2300/414* (2013.01); *A61L 2300/64* (2013.01); *C08G 69/10* (2013.01); *C08L 77/04* (2013.01); *C12N 2537/10* (2013.01)

(58) Field of Classification Search
CPC .... A61K 47/34; A61K 38/18; A61K 38/1816; A61K 38/1825; A61K 38/1833; A61K 38/1841; A61K 38/185; A61K 38/1858; A61K 38/1866; A61K 38/1875; A61K 38/193; A61K 38/30; A61K 38/1808; C08B 37/0075; C08B 37/0072; C08L 77/04; C08L 5/08; C08L 89/06; C12N 2537/10; C12N 5/0068; A61L 27/52; A61L 24/102; A61L 27/24; A61L 24/104; A61L 27/222; A61L 2300/414; A61L 27/38; A61L 2300/64; A61L 27/3834; C09J 105/08; C08H 1/06; C08G 69/10
See application file for complete search history.

(56) References Cited

U.S. PATENT DOCUMENTS

| | | |
|---|---|---|
| 5,512,291 A | 4/1996 | Li |
| 6,090,996 A | 7/2000 | Li |

(Continued)

FOREIGN PATENT DOCUMENTS

JP     1996325160     * 10/1996

OTHER PUBLICATIONS

Kale RN, Bajaj AN, Ultraviolet Spectrophotometric Method for Determination of Gelatin Crosslinking in the Presence of Amino Groups, 1990, J. Young Pharm., vol. 2, No. 1, pp. 90-94 (Year: 1990).*

(Continued)

*Primary Examiner* — David W Berke-Schlessel
*Assistant Examiner* — Trent R Clarke
(74) *Attorney, Agent, or Firm* — Morse, Barnes-Brown & Pendleton, P.C.; Jeannie Wu, Esq.

(57) ABSTRACT

A cell tissue gel, comprising one or more matrix molecules cross-linked with a cross-linking agent, and a quenching agent bound to a reactive group of the cross-linking agent, wherein the quenching agent contains a moiety that is capable of reacting with the reactive group of the cross-linking agent and the one or more matrix molecules contain one or more functional groups that are capable of cross-linking with the reactive group, the amount of the reactive group of the cross-linking agent being equal to or less than a total amount including the amount of the one or more functional groups and the amount of the moiety.

13 Claims, No Drawings

Related U.S. Application Data continuation of application No. 13/167,274, filed on Jun. 23, 2011, now abandoned.

(51) Int. Cl.

| | |
|---|---|
| *A61L 27/24* | (2006.01) |
| *A61L 27/38* | (2006.01) |
| *A61L 27/44* | (2006.01) |
| *A61L 27/52* | (2006.01) |
| *A61L 27/54* | (2006.01) |
| *C08B 11/02* | (2006.01) |
| *C08B 11/12* | (2006.01) |
| *C08B 15/00* | (2006.01) |
| *C08B 15/10* | (2006.01) |
| *C08B 37/00* | (2006.01) |
| *C08B 37/08* | (2006.01) |
| *C08G 12/46* | (2006.01) |
| *C08H 1/00* | (2006.01) |
| *C08H 1/06* | (2006.01) |
| *C08L 5/08* | (2006.01) |
| *C08L 89/06* | (2006.01) |
| *C09J 105/08* | (2006.01) |
| *C12N 5/00* | (2006.01) |
| *C08G 69/10* | (2006.01) |
| *C08L 77/04* | (2006.01) |

(56) References Cited

U.S. PATENT DOCUMENTS

| | | |
|---|---|---|
| 2004/0138695 A1 | 7/2004 | Li et al. |
| 2005/0027069 A1 | 2/2005 | Rhee et al. |
| 2006/0068013 A1 | 3/2006 | DiTizio et al. |
| 2008/0089940 A1 | 4/2008 | Omidian et al. |
| 2009/0075933 A1 | 3/2009 | Basu et al. |
| 2009/0305415 A1 | 12/2009 | Huang |
| 2010/0063253 A1* | 3/2010 | Lin .................. C07K 14/78 530/356 |
| 2010/0099623 A1 | 4/2010 | Schroeder et al. |
| 2010/0214815 A1 | 8/2010 | Tam et al. |
| 2011/0091550 A1 | 4/2011 | Zhang et al. |
| 2011/0150823 A1 | 6/2011 | Huang |
| 2012/0014939 A1 | 1/2012 | Vilallonga et al. |
| 2012/0328557 A1* | 12/2012 | Huang .................. A61L 27/24 514/8.4 |

OTHER PUBLICATIONS

"Amine-Reactive Crosslinker Chemistry" is pdf of webpage at https://www.thermofisher.com/us/en/home/life-science/protein-biology/protein-biology-learning-center/protein-biology-resource-library/pierce-protein-methods/amine-reactive-crosslinker-chemistry.html #2, accessed Aug. 15, 2021 (Year: 2021).*

Joseph R. Kanagy, Chemistry of Collagen, 1947, Circular of the National Bureau of Standards C458, United States Government Printing Office, Washington, D.C., USA, pp. 1-28 (Year: 1947).*

Chang et al "A Genipin-Crosslinked Gelatin Membrane as Wound-Dressing Material: In Vitro and In Vivo Studies" Journal of Biomaterials Science: Polymer Edition vol. 14, pp. 481-495, 2003.

Chiono et al "Genipin-Crosslinked Chitosan/Gelatin Blends for Biomedical Applications" Journal of Materials Science: Materials in Medicine vol. 19, pp. 889-898, 2008.

Jung et al "Ex Vivo Expansion of Human Mesenchymal Stem Cells in Defined Serum-Free Media" Stem Cells International vol. 2012, pp. 1-21, 2012.

Layman et al "The Effect of the Controlled Release of Basic Fibroblast Growth Factor from Ionic Gelatin-Based Hydrogels on Angiogenesis in a Murine Critical Limb Ischemic Model" Biomaterials vol. 28, pp. 2646-2654, 2007.

Mao et al "The Properties of Chitosan-Gelatin Membranes and Scaffolds Modified with Hyaluronic Acid by Different Methods" Biomaterials vol. 24, pp. 1621-1629, 2003.

Shu et al "In Situ Crosslinkable Hyaluronan Hydrogels for Tissue Engineering" Biomaterials vol. 25, pp. 1339-1348, 2004.

Sung et al "Feasibility Study of a Natural Crosslinking Reagent for Biological Tissue Fixation" Journal of Biomedical Materials Research vol. 42, pp. 560-567, 1998.

Sung et al "Felatin-Derived Bioadhesives for Closing Skin Wounds: An In Vivo Study" Journal of Biomaterials Science: Polymer Edition vol. 10, pp. 751-771, 1999.

Falanga et al., "Topically Applied Recombinant Tissue Plasminogen Activator for the Treatment of Venous Ulcers", Phlebology 1996, 22: 643-644.

Jha, A.K. et al., "Molecular weight and concentration of heparin in hyaluronic acid-based matrices modulates growth factor retention kinetics and stem cell fate", Journal of Controlled Release, 209:308-316, 2015.

* cited by examiner

ADHESIVE CELL TISSUE GELS

CROSS REFERENCE TO RELATED APPLICATIONS

This application is a continuation-in-part of U.S. patent application Ser. No. 14/146,260, filed on Jan. 2, 2014, which is a continuation of U.S. patent application Ser. No. 13/167,274, filed on Jun. 23, 2011. The contents of all prior applications are hereby incorporated by reference herein in their entirety.

BACKGROUND OF THE INVENTION

Cell tissue gels with adhesive properties have a wide variety of application. Typically, such gels are formed by using cross-linking agents. However, cross-linking agents can be toxic. There is a need for cell tissue gels with reduced toxicity.

Currently available surgical tissue adhesives can be categorized as either fibrin tissue adhesives or cyanoacrylates. Although fibrin tissue adhesives and cyanoacrylates are often discussed under the general topic of surgical tissue adhesives, these two substances have different indications and mechanisms of action. Fibrin tissue adhesives use naturally occurring substrates that are part of normal endogenous clotting mechanisms. In contrast, the adhesion achieved by cyanoacrylates is a result of synthetic compounds not naturally occurring in the human body. These two types of adhesives also have different clinical indications. Fibrin tissue adhesives are typically applied below the dermis as a biologic hemostat or as a sealant for use with skin grafts and flaps. Cyanoacrylates have been shown to be histotoxic when applied below the dermis and have been used most successfully at the level of the epidermis for superficial skin closure.

Cyanoacrylate-induced histotoxicity results from biodegradation of the polymer into cyanoacetate and formaldehyde byproducts. Beneath the epidermal layer, both of these substances can be toxic to host tissues and are capable of producing acute and chronic inflammation. Acute inflammation has been documented in the early weeks following application, followed by a chronic inflammation seen as a foreign body giant cell reaction.

Tissue gels adhesives may consist of a variety of substances, include proteins and carbohydrates feature prominently. Proteins such as gelatin and carbohydrates such as starch have been used as general-purpose glues for many years, but typically their performance shortcomings have seen them superseded by synthetic alternatives. Typically, the synthetic tissue gels are formed by using cross-linking agents. However, the cross-linking agents are highly toxic to the cells.

Tissue gel adhesives are natural polymeric materials that act as adhesives and are sometimes used to describe glues formed synthetically from biological monomers such as sugars, or to mean synthetic materials designed to adhere to biological tissues. The tissue gels are of commercial interest because they tend to be biocompatible, i.e. useful for biomedical applications involving skin or other body tissues.

Surgical tissue adhesives continue to evolve as an important technology for facial plastic and reconstructive surgeons. An ideal surgical tissue adhesive must meet the following criteria: strong binding strength, ease of application, tissue biocompatibility, biodegradable byproducts, minimal tissue reactivity, and reasonable cost. Therefore, there is a need for cell tissue gel adhesives with less or no toxicity and prepare easily for biomedical and clinical applications.

SUMMARY OF THE INVENTION

The present invention is based on an unexpected discovery that a cell tissue gel that contains a matrix molecule with a cross-linking agent and includes a quenching agent capable of binding to a reactive group of the cross-linking agent exhibits reduced toxicity.

In one aspect, described herein is a cell tissue gel containing one or more matrix molecules cross-linked with a cross-linking agent, and a quenching agent bound to a reactive group of the cross-linking agent, wherein the quenching agent contains a moiety that is capable of reacting with the reactive group of the cross-linking agent and the one or more matrix molecules contain one or more functional groups that are capable of cross-linking with the reactive group, the amount of the reactive group of the cross-linking agent being equal to or less than a total amount including the amount of the one or more functional groups and the amount of the moiety. The ratio of the amount of the reactive group to the total amount including the amount of the one or more functional groups and the amount of the moiety can be smaller than 1:1 (e.g., 1:2 to 1:500 or 1:5 to 1:100 or 1:10 to 1:10000). In some embodiments, the amount of the reactive group is in excess of the amount of the one or more functional groups. In some embodiments, the ratio of the amount of the reactive group to the amount of the moiety is 1:0.01 to 1:100. In some embodiments, the ratio of the amount of the reactive group to the total amount of the one or more functional group and the moiety is 1:1 to 1:100.

The one or more matrix molecules include, but are not limited to, collagen, hyaluronan, gelatin, fibronectin, elastin, tenacin, laminin, vitronectin, heparan sulfate, chondroitin, chondroitin sulfate, keratan, keratan sulfate, dermatan sulfate, carrageenan, heparin, chitin, chitosan, alginate, agarose, agar, cellulose, methyl cellulose, carboxyl methyl cellulose, and glycogen. In some embodiments, the one or more matrix molecules include one of collagen, hyaluronan, and gelatin.

The cross-linking agent typically possesses at least two functional reactive groups and the two functional groups can be identical or different. Cross-linking agents include, but are not limited to, an epoxide, a polyepoxy compound, a dialdehyde, an imidoester, a N-hydroxysuccinimide ester, a carbodiimide, genipin, a riboflavin, a flavonoid, a maleimide, a haloacetyl, a pyridyl disulfide, a hydrazide, an azide, a diazirine, a 6-maleimidohexanoic acid active ester, disuccinimidyl suberate, bis(sulfosuccinimidyl)suberate, and sulfosuccinimidyl-4-(N-maleimidomethyl)cyclohexane-1-carboxylate. Quenching agents include, but are not limited to, an amine, a sulfhydryl, a carbonyl, a glycol, a carboxyl, an azide, a diamine, an oligoamine, a polyamine, a dicarboxylate, an oligo-carboxylate, a polycarboxylate, a polysulfhydryl, a polyhydroxyl, and a photo-crosslinking compound.

In some embodiments, the cross-linking agent is genipin and the quenching agent is a poly-L-lysine. The poly-L-lysine can have an average molecular weight of greater than 20 kDa, e.g., greater than 99 kDa, or greater than 212 kDa. In some cases, the cross-linking agent is ethylene glycol diglycidyl ether and the quenching agent is water. When the cross-linking agent is ethylene glycol diglycidyl ether, the quenching agent can be a poly-lysine or γ-polyglutamic acid.

The cell tissue gel of this invention can further contain a nutrient for cell growth (e.g., a cell culture medium), a bioactive agent, and/or cells (e.g., stem cells, tissue cells or progenitor cells). The bioactive agent can be a growth factor, e.g., epidermal growth factor, fibroblast growth factor, vascular endothelial growth factor, connective tissue growth factor, platelet-derived growth factor, insulin-like growth factor, nerve growth factor, hepatocyte growth factor, colony-stimulating factor, stem cell factor, keratinocyte growth factor, granulocyte colony-stimulating factor, granulocyte macrophage colony-stimulating factor, glial derived neurotrophic factor, ciliary neurotrophic factor, endothelial-monocyte activating polypeptide, epithelial neutrophil activating peptide, erythropoietin, bone morphogenetic protein, brain-derived neurotrophic factor, BRAK, transforming growth factor beta, and tumor necrosis factor.

In another aspect, described herein is a method of making a non-toxic adhesive cell tissue gel. The method includes mixing one or more matrix molecules with a cross-linking agent or quenching agent to obtain a mixture, and adding a quenching agent or cross-linking agent to the mixture, whereby the non-toxic adhesive cell tissue gel is formed. The cross-linking agent contains a reactive group, the quenching agent contains a moiety that is capable of reacting with the reactive group, and the one or more matrix molecules contain one or more functional groups that are capable of cross-linking with the reactive group. The amounts of the cross-linking agent, quenching agent and one or more matrix molecules mixed to form the gel are such that the amount of the reactive group is equal to or less than a total amount including the amount of the one or more functional groups and the amount of the moiety.

In some embodiments, the ratio of the amount of the reactive group to the amount of the moiety is 1:0.01 to 1:100. In some embodiments, the ratio of the amount of the reactive group to the total amount of the one or more functional groups and the moiety is 1:1 to 1:100.

In yet another aspect, described herein is a non-toxic adhesive cell tissue gel kit. The kit contains one or more matrix molecules, a quenching agent, and a cross-linking agent, wherein the cross-linking agent is selected from a group consisting of an epoxide, a polyepoxy compound, a dialdehyde, an imidoester, a N-hydroxysuccinimide ester, a carbodiimide, genipin, a riboflavin, a flavonoid, a maleimide, a haloacetyl, a pyridyl disulfide, a hydrazide, an azide, a diazirine, a 6-maleimidohexanoic acid active ester, disuccinimidyl suberate, bis(sulfosuccinimidyl)suberate, and sulfosuccinimidyl-4-(N-maleimidomethyl)cyclohexane-1-carboxylate. The cross-linking agent contains a reactive group, the quenching agent contains a moiety that is capable of reacting with the reactive group, and the one or more matrix molecules contain one or more functional groups that are capable of cross-linking with the reactive group. The amounts of the cross-linking agent, quenching agent, and one or more matrix molecule in the kit are such that the amount of the reactive group is equal to or less than a total amount including the amount of the one or more functional groups and the amount of the moiety. In some embodiments, the ratio of the amount of the reactive group to the amount of the moiety is 1:0.01 to 1:100. In some embodiments, the ratio of the amount of the reactive group to the total amount of the one or more functional group and the moiety is 1:1 to 1:100.

In another aspect, described herein is a method of delivering cells (e.g., stem cells, progenitor cells or tissue cells) into a subject, including (i) providing a cell implant containing the cell tissue gel described above and cells, and (ii) placing the cell implant in a site of the subject. Also within the scope of this invention is use of the cell tissue gel in manufacturing a cell implant used in cell delivery.

The details of one or more embodiments of the invention are set forth in the description below. Other features or advantages of the present invention will be apparent from the following detailed description of an example and also from the appended claims.

DETAILED DESCRIPTION OF THE INVENTION

Described herein is a biocompatible cell tissue gel that can support cell growth. The cell tissue gel contains one or more matrix molecules (see below) cross-linked with a cross-linking agent, and a quenching agent bound to a reactive group of the cross-linking agent. The cell tissue gel can also further include a nutrient for cell growth (e.g., a cell culture medium), a bioactive agent, or cells (e.g., stem cells, progenitor cells or tissue cells).

The quenching agent contains a moiety that is capable of reacting with the reactive group of the cross-linking agent and the one or more matrix molecules contain one or more functional groups that are capable of cross-linking with the reactive group. The amount (e.g., number) of the reactive group of the cross-linking agent is less than a total amount including the amount of the one or more functional groups and the amount of the moiety. The ratio of the amount of the reactive group to the total amount including the amount of the one or more functional groups and the amount of the moiety can be greater than 1:1 (e.g., 1:2 to 1:500, 1:5 to 1:100 or 1:10 to 1:10000). In some embodiments, the amount of the reactive group is in excess of the amount of the one or more functional groups.

The reaction between molecules should be equivalent. For example, one reactive group in a cross-linking agent can react with one functional group of a matrix molecule and ten reactive groups in one or more cross-linking agents can react with ten functional groups in a matrix molecule. However, due to stereo- or 3D-structure of a molecule, some of the reactive groups in the cross-linking reagent may be left unreacted and are toxic to cells. Therefore, a quenching agent is used to quench out or react with the unreacted groups in the cross-linking agent. Using a quenching agent is particularly useful when the number of reactive group in the cross-linking agent is in excess of the number of the functional groups in the matrix molecule. Normality (N) is known as the equivalent concentration of a solution. Normality can be used to measure the amount or number of a functional group, reactive group, or moiety present in a molecule or composition based on the same volume of solution.

Matrix Molecule

A matrix molecule (e.g., a macromolecular compound) helps retain cells at an implantation site. It can be an extracellular molecule found in the extracellular matrix. Examples are, but are not limited to, collagen, hyaluronan, gelatin, fibronectin, elastin, tenacin, laminin, vitronectin, polypeptides, heparan sulfate, chondroitin, chondroitin sulfate, keratan, keratan sulfate, dermatan sulfate, carrageenan, heparin, chitin, chitosan, alginate, agarose, agar, cellulose, methyl cellulose, carboxyl methyl cellulose, glycogen and derivatives thereof. In addition, the matrix molecule can be fibrin, fibrinogen, thrombin, and polyglutamic acid, a synthetic polymer (e.g., acrylate, polylactic acid, polyglycolic acid, or poly(lactic-co-glycolic acid). It is preferred that the matrix molecule used in the tissue gel described herein has a high molecular weight so as to increase the viscosity of the gel.

Any of the naturally-occurring collagens or their functional variants can be used for preparing the tissue gel of this invention. At the present time, at least 28 genetically distinct species of collagens have been discovered. Collagen can be easily isolated and purified from collagen-rich tissues such as skin, tendon, ligament, and bone of humans and animals. Methods for isolating and purifying collagen are well known in the art. (See, e.g., U.S. Pat. No. 5,512,291; US Patent Publication 20040138695; Methods in Enzymology, vol. 82, pp. 33-64, 1982; The Preparation of Highly Purified Insoluble Collagen, Oneson, I., et al., Am. Leather Chemists Assoc., Vol. LXV, pp. 440-450, 1970; U.S. Pat. No. 6,090, 996). Collagen can also be prepared by recombinant technology, such as those described by Advanced Tissue Sciences (La Jolla, Calif.) or purchased from various venders (e.g., Fibrogen; South San Francisco, Calif.). One example follows. Bovine deep flexor tendons, with fat and fascia removed, are washed with water, frozen, and sliced into 0.5 mm slices with a slicer. A suitable amount of the sliced tendons is first extracted with 50 ml of water at room temperature for 24 hours. The water-soluble fraction is discarded and the sliced tendons are then extracted with an acidic solution (e.g., 0.2 N HCl) at a suitable temperature (e.g., room temperature) for a suitable period of time (e.g., 12-24 hours). The HCl solution is discarded; the tendons rinsed with water to remove the residual acid. The rinsed tendons are then extracted with a basic solution (e.g., 0.75 M NaOH) at a suitable temperature (e.g., room temperature) for a suitable period of time (e.g., 12-24 hours). After discarding the basic solution, the sliced tendons are neutralized with an acidic solution (e.g., 0.1 N HCl) to a pH of 4-7 (e.g. 5) followed by repetitive washes with water to remove the residual base in the tendons. The tendons are then defatted with an alcohol (e.g., isopropanol) for a sufficient period (e.g., 16 hours) at room temperature. The extractant is decanted and the tendons are further extracted with an alcohol (e.g., isopropanol) for a suitable period (e.g., 12-24 hours) at room temperature to form a collagen-containing solution, which can be dried under a clean hood. The collagen powder thus formed can be dispersed in an acidic solution (e.g., 0.5 M or 0.25 M acetic acid) in the presence of a proteolytic enzyme (e.g., trypsin or pepsin) and incubated at 4° C. for a suitable period. The mixture is then filtered through a 100 mesh stainless steel mesh filter and the solubilized collagen can be precipitated with a 5% NaCl solution. The precipitated collagen can be redissolved in the acidic solution described above and the solution thus formed can be filtered through a 100 mesh stainless steel mesh filter to eliminate non-solubilized particles. The collagen solution is then dialyzed with distilled water to remove the acid.

The term "hyaluronan" refers to a naturally-occurring anionic, non-sulfated glycosaminoglycan including repeated disaccharide units of N-acetylglucosamine and D-glucuronic acid, and its derivatives. Naturally-occurring hyaluronan (also known as hyaluronic acid or hyaluronate) can be isolated from its natural sources, e.g., capsules of *Streptococci*, rooster comb, cartilage, synovial joints fluid, umbilical cord, skin tissue and vitreous of eyes, via conventional methods. See, e.g., Guillermo Lago et al. Carbohydrate Polymers 62(4): 321-326, 2005; and Ichika Amagai et al. Fisheries Science 75(3): 805-810, 2009. Alternatively, it can be purchased from a commercial vendor, e.g., Genzyme Corporation, Lifecore Biomedical, LLC and Hyaluron Contract Manufacturing. Derivatives of naturally-occurring hyaluronan include, but are not limited to, hyaluronan esters, adipic dihydrazide-modified hyaluronan, hyaluronan amide products, crosslinked hyaluronic acid, hemiesters of succinic acid or heavy metal salts thereof hyaluronic acid, partial or total esters of hyaluronic acid, sulphated hyaluronic acid, N-sulphated hyaluronic acid, and amines or diamines modified hyaluronic acid. They can be obtained by chemically modifying one or more of its functional groups (e.g., carboxylic acid group, hydroxyl group, reducing end group, N-acetyl group). A carboxyl group can be modified via esterification or reactions mediated by carbodiimide and bishydrazide. Modifications of hydroxyl groups include, but are not limited to, sulfation, esterification, isourea coupling, cyanogen bromide activation, and periodate oxidation. A reducing end group can be modified by reductive amination. It also can be linked to a phospholipid, a dye (e.g., a fluorophore or chromophore), or an agent suitable for preparation of affinity matrices. Derivatives of naturally-occurring hyaluronan can also be obtained by crosslinking, using a crosslinking agent (e.g., bisepoxide, divinylsulfone, biscarbodiimide, small homobifunctional linker, formaldehyde, cyclohexyl isocyanide, and lysine ethyl ester, metal cation, hydrazide, or a mixture thereof) or via internal esterification, photocross-linking, or surface plasma treatment.

It has been shown that hyaluronan, particularly hyaluronan of high molecular weight (i.e., greater than 5 kDa), is effective in promoting angiogenesis, thereby facilitating wound recovery. See U.S. Provisional Application No. 61/390,789. To practice this invention, the hyaluronan can have a molecular weight of 5 kDa to 5,000 kDa (e.g., 7 kDa to 1,500 kDa, 200 kDa to 1,500 kDa, 500 kDa to 1,500 kDa, or 700 kDa to 1,500 kDa).

Also, it has been shown that cells or stem cells display improved viability when growing in a cell tissue gel that contains collagen and hyaluronan at particular weight ratios of 0.01-100 (collagen):1 (hyaluronan). See U.S. application Ser. No. 12/974,535. To make the cell tissue gel described herein, the concentration of the hyaluronan can be 0.001 to 100 mg/ml (e.g., 0.01 to 1 mg/ml) and that of the collagen can be 0.001 to 100 mg/ml. Preferably, the collagen concentration is 0.1 to 100 mg/ml and the hyaluronan concentration is 0.01 to 35 mg/ml. More preferably, the collagen concentration is 3-75 mg/ml (e.g., 6 mg/ml or 9 mg/ml) and the hyaluronan concentration is 0.2-75 mg/ml.

Cross-Linking Agent

A cross-linking agent is capable of reacting with target molecules and links the target molecules together. A cross-linking agent typically contains at least two reactive groups that can react with functional groups of the target molecules. Table 1 below shows exemplary reactive groups and functional groups. Cross-linking agents and reactive groups are well known in the art.

Cross-linking agents useful in the present invention include, but are not limited to, an imidoester, an epoxide (e.g., ethylene glycol diglycidyl ether), a dialdehyde (e.g., glutaraldehyde), a N-hydroxysuccinimide ester (e.g., 2,3-dibromopropionyl-N-hydroxysuccinimide ester, Sulfo-N-hydroxysuccinimide ester, and chlorambucil-N-hydroxysuccinimide ester), a carbodiimide (e.g., 1-ethyl-3-(3-dimethylaminopropyl) carbodiimide hydrochloride), genipin, a maleimide, a haloacetyl, a pyridyl disulfide, a hydrazide, a riboflavin, a bioflavonoid, a flavonoid (e.g., proanthocyanidin, catechin, epicatechin, epigallo catechin, epicatechin gallate, epigallocatechin gallate, quercetin, chalcones, apigenin, luteolin, a polymethoxylated flavone, quercitol, kaempferol, myricetin, an anthocyanin, resveratrol, an isoflavonoid, daidzein, genistein, nobiletin, tangeretin, and tannic acid), a 6-maleimidohexanoic acid active ester, disuccinimidyl suberate, bis(sulfosuccinimidyl)suberate, an azide, a diazirine, sulfosuccinimidyl-4-(N-maleimidomethyl)cyclohexane-1-carboxylate, and derivatives thereof. A cross-linking agent can also be a polymer containing multiple identical or different functional reactive groups, e.g., a polyepoxy compound, and a poly(hydroxy acid).

TABLE 1

Reactive groups and their target functional groups.

| Reactive Group | Target Functional Group |
| --- | --- |
| Aryl Azide | Nonselective (or primary amine) |
| Carbodiimide | Amine/Carboxyl |
| Carbonyl | Hydrazine |
| Diazirine | Nonselective |
| Hydrazide | Carbohydrate (oxidized) |
| Hydroxymethyl Phosphine | Amine |
| Imidoester | Amine |
| Isocyanate | Hydroxyl (non-aqueous) |
| Maleimide | Sulfhydryl |
| NHS-ester | Amine |
| PFP-ester | Amine |
| Psoralen | Thymine (photoreactive intercalator) |
| Pyridyl Disulfide | Sulfhydryl |
| Vinyl Sulfone | Sulfhydryl, amine, hydroxyl |

Quenching Agent

A quenching agent is an agent capable of reacting with a reactive group of a cross-linking agent. When target molecules are cross-linked with a cross-linking agent, a quenching agent can be used to react with reactive groups of the cross-linking agent that have not reacted with the functional groups of the target molecules. By "using-up" the free reactive groups, a quenching agent can fully or partially reduce the toxicity of the cross-linking agent. A quenching agent can be a compound that contains an amine, a sulfhydryl, a carbonyl, a glycol, a carboxyl, an azide or a photocrosslinking group. In other words, a quenching agent contains a moiety that can react with a reactive group of a cross-linking agent. For example, for a cross-linking agent with an amine reactive group, the quenching agents include, but are not limited to, diamines, oligoamines, and polyamines such as polylysine and polyglutamine. For a cross-linking agent with a carboxyl reactive group, a useful quenching agent can be a dicarboxylic acid, an oligo-carboxylic acid, or a polycarboxylic acid such as poly-glutamate or poly-glutamic acid. Other exemplary quenching agents include polysulfhydryl-containing compounds, which can be used to quench sulfhydryl reactive groups, and polyhydroxy-containing compounds, which can be used to quench hydroxyl reactive groups.

Nutrient for Cell Growth

The term "nutrient" refers to a source of nourishment essential for cell growth. It can be amino acid, vitamin, mineral, carbon source (e.g., glucose), fatty acid, or a mixture thereof. In one example, the nutrient used in the tissue gel of this invention is a cell growth medium, e.g., Minimum Essential Medium, Basal Medium Eagle, Dulbecco's Modified Eagle's medium, Ham's Nutrient Mixtures F-10 or F-12, Medium 199, RPMI medium, Ames' Media, BGJb Medium (Fitton-Jackson Modification), Click's Medium, CMRL-1066 Medium, Fischer's Medium, Glascow Minimum Essential Medium, Iscove's Modified Dulbecco's Medium, L-15 Medium, McCoy's 5A Modified Medium, NCTC Medium, Swim's S-77 Medium, Waymouth Medium, or William's Medium E.

Bioactive Agent

Any agent (e.g., peptide, polypeptide, oligosaccharide, polysaccharide, or small molecule) that improves cell viability, promotes cell proliferation, or induces cell differentiation can be used in making the tissue gel of this invention. In one example, the bioactive agent is a growth factor, such as epidermal growth factor, fibroblast growth factor, vascular endothelial growth factor, connective tissue growth factor, platelet-derived growth factor, insulin-like growth factor, nerve growth factor, hepatocyte growth factor, colony-stimulating factors, stem cell factor, serotonin, and von Willebrand factor, transforming growth factor, keratinocyte growth factor, granulocyte colony-stimulating factor, granulocyte/macrophage colony stimulating factor, glial derived neurotrophic factor, ciliary neurotrophic factor, endothelial-monocyte activating polypeptide, epithelial neutrophil activating peptide, erythropoietin, bone morphogenetic proteins, brain-derived neurotrophic factor. In another example, the bioactive agent is a cytokine or chemokine, including, but are not limited to, IL-2, breast-expressed chemokine (e.g., BRAK), kidney-expressed chemokine (e.g., CXCL14). The bioactive agent can also be a cell differentiation factor, such as dexamethasone, sodium pyruvate, ascorbic acid-2-phosphate, retinoic acid, proline, insulin, transferrin, selenous acid, linoleic acid, and bovine serum albumin, and TGF-$\beta$3. In a preferred example, the differentiation factor is a compound that promotes chondrogenesis of mesenchymal stem cells (see those disclosed in U.S. Pat. No. 5,908,784), osteogenesis (e.g., dexamethasone, ascorbic acid, $\beta$-glycerol phosphate), adipogenesis (e.g., insulin, isobutyl-methyl xanthine, dexamethasone, indomethacin), cardiomyogenic differentiation (e.g., activin A, BMP-4), endothelial cell differentiation (e.g., EBM-2, dexamethasone, and VEGF), smooth muscle cell differentiation (e.g., PDGF-BB), neural induction (e.g., bFGF, EGF, and B27 supplement, DMSO, butylated hydroxyanisole, forskolin, valproic acid, KCl, K252a, and N2 supplement) and endodermal lineage differentiation (e.g., dexamethasone, HGF, and FGF-4). The bioactive agent can also be a Chinese herbal medicine or an active ingredient thereof.

Preparation of Tissue Gels

The tissue gel described herein can be prepared by mixing all of its components mentioned above at a desired normality ratio and keeping the mixture under suitable conditions to allow gel formation. For example, one or more matrix molecules can be first mixed with a quenching agent to obtain a mixture and a cross-linking agent can be added to the mixture to form a gel. Alternatively, one or more matrix molecules can be first mixed with a cross-linking agent to obtain a mixture, and a quenching agent can be added immediately to the mixture to form a gel. Other components can be added prior to gel formation.

To prepare a cell-embedded gel, desired cells can be mixed with the gel components prior to gel formation. The cells can be tissue cells or stem cells obtained from a mammal (e.g., bovine, porcine, murine, equine, canine, feline, ovine, simian, and human). Examples are, but are not limited to, placenta-derived stem cells, bone marrow-derived stem cells, stromal cells (e.g., adipose-derived stromal cells), mesenchymal stem cells, tissue progenitor cells, blast cells, or fibroblasts.

The tissue gel thus prepared, with or without cells embedded, can be implanted to a desired site for tissue repair and other therapeutic purposes.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever.

Example 1: Crosslinked Tissue Gels Containing Poly-L-Lysine (A) Materials and Methods The quenching agents tested in the study include spermine, protamine, 1,6-hexanediamine, poly-L-lysine with different sets of molecular weights. The average molecular weights of the poly-L-lysine were 3.4, 20, 99, 212 and 225 kDa.

Equal normality of each of the polyamines was premixed with gelatin (300 mg/mL) in a phosphate buffered saline solution. Equal volume of a genipin solution at 20 mg/mL and the above polyamine-gelatin solution were mixed before applying to the dermal side of a pig skin sample (10×30× 0.7~0.9 mm$^3$) to form an adhesive. A weight of 50 gm was placed on the area with the adhesive (1×1 cm$^2$) for 30 minutes. The bounding strength of the adhesive was measured using the LRX Material Testing System (Lloyd Instruments Ltd., England) at a separation rate of 10 mm/min.

The cytotoxic effect of the adhesive was evaluated by applying 10 μL of the adhesive to the center of a well of a 24-well plate. Fibroblasts (2.0×10$^4$ cell/well) were seeded and incubated at 37° C. with 5% $CO_2$ for 38 hours. The number of viable cells was quantified by a hemacytometer.

The rheological properties of the adhesives in the presence and absence of the poly-L-lysine were measured by a set of cone and cup using a RheoStress RS 150 (Haake, Germany). The elastic storage modulus (G') in real time was recorded along with time at fixed shear stress (1 Pa) and frequency (1 Hz). The effects of reaction temperature on G' were also monitored.

(B) Bounding Strength

The results demonstrate that polyamines at molecular weight above 20 kDa improved the bounding strength of the adhesives. Poly-L-lysine at molecular weight of 212 kDa was chosen to perform further studies. These further studies showed that the bounding strength of an adhesive with the poly-L-lysine increased along with elevated concentration of poly-L-lysine until 46.8 mN. Studies done with an adhesive made with 17.5 mN poly-L-lysine and one without any polylysine showed that the maximum bounding strength of an adhesive with the polylysine is higher than one without the polylysine.

Elevated bounding strengths of the adhesive were observed with increased amounts of poly-L-lysine regardless of the concentration of genipin. In addition, the bounding strength was enhanced with raised concentration of genipin.

(C) Toxicity

Cytotoxicity of the adhesive in the absence of poly-L-lysine was increased with elevated concentration of genipin. The addition of poly-L-lysine significantly reduced the cytotoxic effects of genipin. No significant cytotoxic effect was observed with 7.5 mg/mL of genipin together with 46.8 mN of a poly-L-lysine.

(D) Rheological Properties

To further understand the influence of the poly-L-lysine on the physical and chemical properties of the adhesive, the elastic storage modulus (G') in real time was monitored. Through the oscillation test with fixed shear stress (1 Pa) and frequency (1 Hz), the G' value increased along with the formation of the adhesive from a liquid state. The G' value was significantly higher with the addition of poly-L-lysine to the adhesive. The G' values at different reaction temperatures were monitored and a steep increase at about 90 minutes was observed with the reaction carried out 50° C. The phase transition indicated that the poly-L-lysine was involved in the cross-linking reaction of the adhesive and greatly increased the elastic modulus of the adhesive. The phase transition was not observed in the absence of the poly-L-lysine.

Example 2: Toxicities of Gels Prepared with Different Crosslinking Agents and Quenching Agents Gels containing various ratios of reactive groups in crosslinking agents to those in the matrix molecules with quenching agents were prepared as indicated in Table 2. Normality was used to indicate the number of reactive groups in the crosslinking agents, the number of functional groups in the matrix molecules, or the number of moieties in the quenching agents. Live cells were seeded and added to the gels, and cell viability was observed. Crosslinking agents were divided into two groups: highly toxic and less toxic. Glutaraldehyde was one of the highly toxic crosslinking agents and epoxide and genipin were the less toxic crosslinking agents. The quenching agents tested were poly-L-lysine and γ-polyglutamic acid.

When cultured for 24 hours, it was found that most cells died in the presence of more than 0.5 mN of highly toxic crosslinking agents such as glutaraldehyde and only about 20% of the cells survived at 0.1 mN. While more than 50% of the cells were alive in the presence of 1 mN of less toxic crosslinking agents such as epoxide, all cells died at 5 mN of crosslinking agents.

TABLE 2

Viability of cells in contact with various concentrations of each individual crosslinking agent or various mixtures with different Normality ratios of reactive groups in crosslinking agents to functional groups in the matrix molecules and moieties in quenching agents

| crosslinking agents | crosslinking agent only | | Normality ratios of reactive groups in crosslinking agents to functional groups in the matrix molecules and quenching agents | | | | |
|---|---|---|---|---|---|---|---|
| | | | 1:1 | 1:5 | 1:10 | 1:50 | 1:100 |
| glutaraldehyde | ≥0.5 mN All die | 0.1 mN ~20% alive | Adjacent cells die | Some cells die | 100% alive | 100% alive | 100% alive |

TABLE 2-continued

Viability of cells in contact with various concentrations of each individual crosslinking agent or various mixtures with different Normality ratios of reactive groups in crosslinking agents to functional groups in the matrix molecules and moieties in quenching agents

| crosslinking agents | crosslinking agent only | | Normality ratios of reactive groups in crosslinking agents to functional groups in the matrix molecules and quenching agents | | | | |
|---|---|---|---|---|---|---|---|
| | ≥5 mN | 1 mN | 5:1 | 1:1 | 1:5 | 1:10 | 1:50 |
| epoxide | All die | ≥70% alive | All die | Some cells die | 100% alive | 100% alive | 100% alive |
| genipin | ≥5 mN | 1 mN | 5:1 | 1:1 | 1:5 | 1:10 | 1:50 |
| | All die | ≥80% alive | All die | Some cells die | 100% alive | 100% alive | 100% alive |

For highly toxic crosslinking agents, cells only survived at concentrations 10 times lower than those of the less toxic crosslinking agents. In the presence of quenching agents, cells survived at the ratio of 1:5 (amount of reactive groups in cross-linking agents:total amount of functional groups in matrix molecules and moieties in quenching agents) with highly toxic crosslinking agents, while the survival ratio was 1:1 for less toxic crosslinking agents.

In another word, with highly toxic crosslinking agents, it required five times more functional groups in the matrix molecules and moieties in quenching agents combined than those in less toxic crosslinking agents to neutralize or overcome the toxicity due to the crosslinking agents.

The above results were summarized from various sets of experiments. Specifically, final concentrations of 0.1 mN, 0.5 mN, 1 mN, and 5 mN of glutaraldehyde were tested alone or added to a gelatin or collagen solution in the presence of poly-L-Lysine as a quenching reagent. When 5 mN of glutaraldehyde was added to a total 5 mN of collagen and poly-L-lysine, most adjacent cells died within 48 hours of observation. When 0.5 mN of glutaraldehyde was mixed with a total of 5 mN of collagen and poly-L-lysine, fibroblasts survived and proliferated like the control groups. For the epoxide groups, all fibroblasts died in the gel made with 25 mN EX-810 and a total of 5 mN collagen and poly-L-lysine. Only some adjacent fibroblasts died in the gel made with 5 mN EX-810 and a total 5 mN of collagen and poly-L-lysine. For the genipin groups, although some fibroblasts died in the gel made with 5 mN genipin and a total 5 mN of collagen and poly-L-lysine, most fibroblasts survived in the distal area.

Example 3: Toxicities of Gels Prepared with Different Crosslinking Agents

Gels were prepared from collagen with glutaraldehyde, EX-810, and genipin at 5 mN, 1 mN, 0.5 mN, and 0.1 mN, respectively. Out of the three crosslinking agents, glutaraldehyde was the most toxic and genipin was the least toxic. Normality was used to indicate the numbers of reactive groups in the crosslinking agents. NIH3T3 fibroblast cells were cultured with the gels and a culture medium in a 96-well plate at $4 \times 10^4$ cells per well. Cell viability was observed.

It was observed that, for glutaraldehyde, most cells died at 0.5 mN at 24 hours of culturing. At 0.1 mN, only 20% of the cells adhered to the gel. For EX-810, at 5 mN, all cells died. At 1 mN of EX-810, over 70% of the cells survived, but there was no sign of cell proliferation. For genipin, all cells died at 5 mN. At 1 mN of genipin, over 80% of the cells survived, but there was no cell proliferation.

Example 4: Toxicities of Gels Prepared with Different Crosslinking Agents and Poly-L-Lysine Gels were prepared containing various components as shown in Tables 3-5. A gel mixture was placed in a well of a 24-well plate and the plate was incubated at 37° C. until each mixture became gelatinous. NIH3T3 fibroblasts at $2 \times 10^4$ cells/well were seeded in a culture medium and cell viability was observed. Cells cultured on collagen only were used as controls.

At day-3 of culturing, it was observed that groups G1, G2, E1, E2, and N1 had lower number of cells than the controls. All other groups had similar cell numbers as the control groups.

TABLE 3

| | mN | | | | |
|---|---|---|---|---|---|
| Collagen (C) | 3.85 | 3.85 | 3.85 | 3.85 | 3.85 |
| Poly-L-lysine (L) | 1.15 | 1.15 | 1.15 | 1.15 | 1.15 |
| C + L | 5 | 5 | 5 | 5 | 5 |
| Glutaraldehyde | 5 | 1 | 0.5 | 0.1 | 0.05 |
| Ratio (X-linking agent: C + L) | 1:1 | 1:5 | 1:10 | 1:50 | 1:100 |
| Group | G1 | G2 | G3 | G4 | G5 |

TABLE 4

| | mN | | | | |
|---|---|---|---|---|---|
| Collagen (C) | 3.85 | 3.85 | 3.85 | 3.85 | 3.85 |
| Poly-L-lysine (L) | 1.15 | 1.15 | 1.15 | 1.15 | 1.15 |
| C + L | 5 | 5 | 5 | 5 | 5 |
| Ex-810 | 25 | 5 | 1 | 0.5 | 0.1 |
| Ratio (X-linking agent: C + L) | 5:1 | 1:1 | 1:5 | 1:10 | 1:50 |
| Group | E1 | E2 | E3 | E4 | E5 |

TABLE 5

| | mN | | | | |
|---|---|---|---|---|---|
| Collagen (C) | 3.85 | 3.85 | 3.85 | 3.85 | 3.85 |
| Poly-L-lysine (L) | 1.15 | 1.15 | 1.15 | 1.15 | 1.15 |
| C + L | 5 | 5 | 5 | 5 | 5 |
| Genipin | 25 | 5 | 1 | 0.5 | 0.1 |
| Ratio (X-linking agent: C + L) | 5:1 | 1:1 | 1:5 | 1:10 | 1:50 |
| Group | N1 | N2 | N3 | N4 | N5 |

Example 5: Cytotoxicity Test of Tissue Gels Containing Different Doses of a Cross-Linking Agent (EX-810)

Collagen at 30 mg/ml (0.33N) was mixed with different concentrations of cross-linking agent EX-810 in a phosphate buffered saline solution as shown in Table 6 to form tissue gels. $3.4 \times 10^4$ placenta-derived mesenchymal stem cells were mixed with the above tissue gels and incubated at 37° C. for 48 hours. Trypan blue at 0.1% and 0.004125% (W/V) of neutral red reagents were used to stain the cells. A three-μL drop of gel containing the cells was placed on a glass slide, and dead cells stained for trypan blue and alive cells stained for neutral red were observed under a microscope. The result was recorded as shown in Table 6.

TABLE 6

| Group | Negative control | No. 1 | No. 2 | No. 3 |
|---|---|---|---|---|
| EX-810 (mN) | 0 | 100 | 10 | 1 |
| Ratio (EX-810:collagen) |  | 1:3.3 | 1:33 | 1:330 |
| Alive cells (%) | 100 | 0 | 60~70 | 80~90 |

Example 6: Cytotoxicity of Adhesive Cell Tissue Gels Formed from Different Doses of a Cross-Linking Agent with a Matrix Molecule and a Quenching Agent In order to reduce cytotoxicity, a quenching agent was introduced. Tissue gels were formed by mixing a matrix molecule such as collagen and a quenching reagent such as polyglutamic acid initially, followed by further mixing with a crosslinking agent such as EX-810 as shown in Table 7. As shown in Table 8, a matrix molecule such as collagen was mixed with a crosslinking agent EX-810 initially, followed by further mixing with a quenching agent such as polyglutamic acid in order to quench or remove cytotoxicity.

Placenta-derived mesenchymal stem cells at $3.4 \times 10^4$ cells/well were seeded on the surface of a tissue culture plate and incubated at 37° C. with 5% of $CO_2$. The cell culture medium of DMEM-10% FBS was removed by suction after cell attachment. Various tissue gels as formulated in Tables 7 and 8 were added to the center on the top of the cells. After the formation of tissue gels, cell medium was added and cultured at 37° C. with 5% of $CO_2$ for another 48 hours. Cell morphology was observed under a microscope and trypan blue was used to stain dead cells. The introduction of a quenching agent to the adhesive cell tissue gels largely reduced cytotoxicity.

TABLE 7

| Group No. | 4 | 5 | 6 | 7 | 8 | 9 |
|---|---|---|---|---|---|---|
| Collagen (C) | 0.45N | 0.45N | 0.45N | 0.45N | 0.45N | 0.45N |
| Polyglutamic acid (P) | 0.05N | 0.05N | 0.05N | 0.05N | 0.05N | 0.05N |
| EX-810 (E) | 0.005N | 0.01N | 0.05N | 0.1N | 0.125N | 0.17N |
| E:(C + P) | 1:100 | 1:50 | 1:10 | 1:5 | 1:4 | 1:3 |

TABLE 8

| Group No. | 10 | 11 | 12 | 13 | 14 | 15 |
|---|---|---|---|---|---|---|
| Collagen (C) | 0.4009N | 0.4009N | 0.3945N | 0.3882N | 0.3821N | 0.3763N |
| EX-810 (E) | 0.0043N | 0.008N | 0.0403N | 0.0794N | 0.1172N | 0.1538N |
| Polyglutamic acid (P) | 0.0409N | 0.0409N | 0.0403N | 0.0396N | 0.039N | 0.0384N |
| E:(C + P) | 1:102 | 1:55 | 1:11 | 1:5 | 1:4 | 1:3 |

Example 7: Adhesive Cell Tissue Gels Formed from Different Matrix Molecules Paired with Quenching Reagent Similar to Tables 7 and 8, adhesive tissue gels were also formed by mixing a matrix molecule of hyaluronan and a quenching reagent such as polyglutamic acid, followed by further mixing with a crosslinking agent such as an epoxide. When the normality of the epoxide was lower than the normality sum of hyaluronan and polyglutamic acid, cytoxicity was minimized or not observed.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A cell tissue gel, comprising one or more matrix molecules cross-linked with a cross-linking agent, and a quenching agent bound to a reactive group of the cross-linking agent, wherein the quenching agent contains a moiety that is capable of reacting with the reactive group of the cross-linking agent and the one or more matrix molecules contain one or more functional groups that are capable of cross-linking with the reactive group, the moiety being in an amount sufficient to react with any reactive group not cross-linked to the one or more functional groups and to reduce the cytotoxicity of the cell tissue gel cross-linked with the cross-linking agent, wherein the quenching agent is a polyglutamic acid and the cross-linking agent is not glutaraldehyde or N-hydroxysuccinimide ester, wherein the cell tissue gel lacks any fibroblast growth factor, and wherein the cytotoxicity of the cell tissue gel is reduced as compared to in the absence of the quenching agent.

2. The cell tissue gel of claim 1, wherein the cross-linking agent is selected from the group consisting of an epoxide, and genipin.

3. The cell tissue gel of claim 1, wherein the one or more matrix molecules are selected from the group consisting of collagen, hyaluronan, gelatin, fibronectin, elastin, tenacin, laminin, vitronectin, heparan sulfate, chondroitin, chondroitin sulfate, keratan, keratan sulfate, dermatan sulfate, carrageenan, heparin, chitin, chitosan, alginate, agarose, agar, cellulose, methyl cellulose, carboxyl methyl cellulose, and glycogen.

4. The cell tissue of claim 3, wherein the one or more matrix molecules are selected from the group consisting of collagen, hyaluronan, and gelatin.

5. The cell tissue gel of claim 1, further comprising a nutrient, a bioactive agent, or both.

6. The cell tissue gel of claim 5, wherein the nutrient is a cell culture medium.

7. The cell tissue gel of claim 5, wherein the bioactive agent is a growth factor selected from the group consisting of epidermal growth factor, vascular endothelial growth factor, connective tissue growth factor, platelet-derived growth factor, insulin-like growth factor, nerve growth factor, hepatocyte growth factor, colony-stimulating factor, stem cell factor, keratinocyte growth factor, granulocyte colony-stimulating factor, granulocyte macrophage colony-stimulating factor, glial derived neurotrophic factor, ciliary neurotrophic factor, endothelial-monocyte activating polypeptide, epithelial neutrophil activating peptide, erythropoietin, bone morphogenetic protein, brain-derived neurotrophic factor, BRAK, transforming growth factor beta, and tumor necrosis factor.

8. The cell tissue gel of claim 1, further comprising cells.

9. The cell tissue gel of claim 2, wherein the cross-linking agent is an epoxide.

10. The cell tissue gel of claim 9, wherein the one or more matrix molecules are selected from the group consisting of collagen, hyaluronan, and gelatin.

11. The cell tissue gel of claim 9, wherein the quenching agent is γ-polyglutamic acid and the one or more matrix molecules are selected from the group consisting of collagen, hyaluronan, and gelatin.

12. The cell tissue gel of claim 1, wherein the cell tissue gel lacks any growth factor.

13. The cell tissue gel of claim 1, wherein the one or more matrix molecules do not include a synthetic polymer or an acrylate.

* * * * *